(12) United States Patent
Barth et al.

(10) Patent No.: US 7,138,424 B2
(45) Date of Patent: Nov. 21, 2006

(54) INDOLE DERIVATIVES, METHOD FOR PREPARING SAME AND PHARMACEUTICAL COMPOSITIONS CONTAINING SAME

(75) Inventors: Francis Barth, Saint-Georges d'Orques (FR); Carole Guillaumont, Aigues-Vives (FR); Murielle Rinaldi-Carmona, Saint-Georges d'Orques (FR); Claude Vernhet, Le Triadou (FR)

(73) Assignee: Sanofi-Aventis, Paris (FR)

( * ) Notice: Subject to any disclaimer, the term of this patent is extended or adjusted under 35 U.S.C. 154(b) by 165 days.

(21) Appl. No.: 10/514,309

(22) PCT Filed: May 15, 2003

(86) PCT No.: PCT/FR03/01470

§ 371 (c)(1),
(2), (4) Date: Nov. 12, 2004

(87) PCT Pub. No.: WO03/097597

PCT Pub. Date: Nov. 27, 2003

(65) Prior Publication Data

US 2006/0089345 A1    Apr. 27, 2006

(30) Foreign Application Priority Data

May 17, 2002    (FR) .................................. 02 06133

(51) Int. Cl.
*A61K 31/404* (2006.01)
*C07D 209/14* (2006.01)
(52) U.S. Cl. ....................................... 514/415; 548/491
(58) Field of Classification Search ................. 548/491
See application file for complete search history.

(56) References Cited

U.S. PATENT DOCUMENTS 6,013,648 A    1/2000    Rinaldi et al.

FOREIGN PATENT DOCUMENTS

WO    WO97/00860    1/1997
WO    WO01/28557    4/2001

*Primary Examiner*—Joseph K. McKane
*Assistant Examiner*—Jason M. Nolan
(74) *Attorney, Agent, or Firm*—Balaram Gupta

(57) ABSTRACT

The present invention provides compounds of formula:

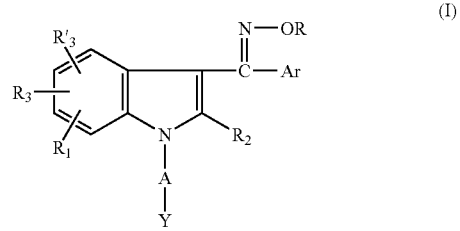

and also provides their preparation and the pharmaceutical compositions comprising them. These compounds are ligands of $CB_2$ cannabinoid receptors.

8 Claims, No Drawings

INDOLE DERIVATIVES, METHOD FOR PREPARING SAME AND PHARMACEUTICAL COMPOSITIONS CONTAINING SAME

This application is the U.S. National Phase of PCT/FR03/01470, filed May 15, 2003, and claims priority to France 02/06133, filed May 17, 2002, of which are incorporated herein by reference in their entirety.

The present invention relates to new compounds derived from indole which are ligands of $CB_2$ cannabinoid receptors, to the process for preparing them and to the pharmaceutical compositions comprising them.

$\Delta^9$-THC is the principal active constituent extracted from *Cannabis sativa* (Tuner, 1985; In Marijuana 1984, Ed. Harvey, D Y, IRL Press, Oxford).

Numerous articles have described not only psychotropic effects of the cannabinoids but also their influence on the immune function [Hollister L. E., J. Psychoact. Drugs 24 (1992), 159–164]. Most of the in vitro studies have shown immunosuppressant effects for the cannabinoids: inhibition of the proliferative responses of T lymphocytes and B lymphocytes, induced by mitogens [Luo, Y. D. et al., Int. J. Immunopharmacol. (1992) 14, 49–56, Schwartz, H. et al., J. Neuroimmunol. (1994) 55, 107–115], inhibition of the activity of cytotoxic T cells [Klein et al., J. Toxicol. Environ. Health (1991) 32, 465–477], inhibition of the microbicidal activity of macrophages and of the synthesis of TNFα [Arata, S. et al., Life Sci. (1991) 49, 473–479; Fisher-Stenger et al. J. Pharm. Exp. Ther. (1993) 267, 1558–1565], inhibition of the cytolytic activity and of the production of TNFα on the part of large granular lymphocytes [Kusher et al. Cell. Immun. (1994) 154, 99–108]. In some studies amplification effects were observed: an increase in the bioactivity of interleukin-1 by resident mouse macrophages or differentiated macrophage cell lines, caused by increased levels of TNFα [Zhu et al., J. Pharm. Exp. Ther. (1994) 270, 1334–1339; Shivers, S. C. et al. Life Sci. (1994) 54, 1281–1289].

The effects of the cannabinoids are due to an interaction with specific high-affinity receptors, coupled to G proteins, present centrally (Devane et al., Molecular Pharmacology (1988), 34, 605–613) and peripherally (Nye et al., J. Pharmacol. and Exp. Ther. (1985), 234, 784–791; Kaminski et al., Molecular Pharmacol. (1992), 42, 736–742; Munro et al., Nature (1993), 365, 61–65).

The central effects of the cannabinoids relate to a first type of cannabinoid receptors ($CB_1$) which is present primarily in the brain but also in the periphery. Moreover, Munro et al. [Nature (1993) 365, 61–65] cloned a second type of cannabinoid receptor, called $CB_2$, which is present in the periphery and more particularly on cells of immune origin. The presence of $CB_2$ cannabinoid receptors on lymphoid cells may explain the abovementioned immunomodulation exerted by cannabinoid receptor agonists.

Certain indole derivatives have been cited in the prior art as exhibiting an affinity for $CB_2$ receptors. Thus patent U.S. Pat. No. 5,532,237 describes compounds of formula:

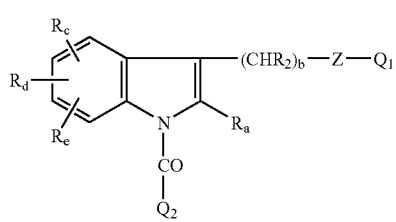

(A)

in which the substituents have various values; and patent application EP 833 818 describes compounds of formula:

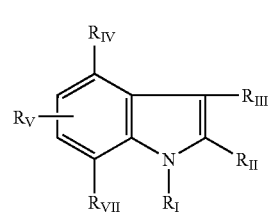

(B)

in which the substituents have various values.

Moreover, patent U.S. Pat. No. 4,581,354 describes indole derivatives which are active as analgesics and antiinflammatories, of formula:

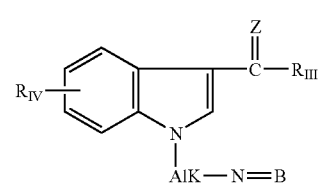

(C)

in which Z may represent oxygen or an NOH group.

The present invention provides compounds of formula:

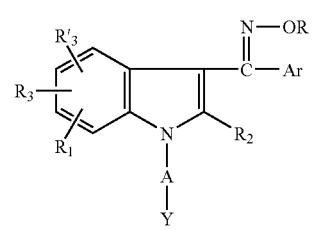

(I)

in which:

Ar represents:
a) a phenyl which is mono-, di- or trisubstituted by one or more groups selected from the following: a halogen atom, a $(C_1–C_4)$alkyl, a trifluoromethyl, an amino, a nitro, a hydroxyl, a $(C_1–C_4)$alkoxy, a $(C_1–C_4)$alkylsulfanyl, a $(C_1–C_4)$alkylsulfonyl;
b) a naphthyl which is unsubstituted or substituted once or twice by a halogen atom, a $(C_1–C_4)$alkyl group or a trifluoromethyl;

A represents a $C_2–C_6$ alkylene radical;

Y represents a group selected from $SR_4$, $SOR_4$, $SO_2R_4$, $SO_2NR_5R_6$, N $(R_7)$ $SO_2R_4$, $OR_4$ and $NR_7SO_2NR_5R_6$;

R represents hydrogen, a $(C_1–C_4)$alkyl or $(C_2–C_4)$alkenyl group or a group $(C_2–C_4)$alk-$NR_8R_9$;

$R_1$, $R_3$ and $R'_3$ represent each independently of one another hydrogen, a halogen atom or a hydroxyl, $(C_1–C_4)$alkyl, trifluoromethyl or $(C_1–C_4)$alkoxy group;

$R_2$ represents hydrogen or a $(C_1–C_4)$alkyl group;

$R_4$ represents a $(C_1–C_4)$alkyl group or a trifluoromethyl;

$R_5$ and $R_6$ represent each independently hydrogen or a $(C_1–C_4)$alkyl group;

$R_7$ represents hydrogen or a $(C_1–C_4)$alkyl group;

R$_8$ and R$_9$ represent each independently of one another hydrogen or a (C$_1$–C$_4$)alkyl group, or R$_8$ and R$_9$ together with the nitrogen atom to which they are connected constitute a heterocyclic radical containing from 4 to 7 ring members and being able to contain another heteroatom selected from a nitrogen, oxygen or sulfur atom, unsubstituted or substituted by one or more methyl or methoxy groups;

and their salts, where appropriate, and their solvates.

By halogen is meant a chlorine, bromine, fluorine or iodine atom.

By (C$_1$–C$_4$)alkyl is meant a linear or branched C$_1$–C$_4$ aliphatic group such as, for example, a methyl, ethyl, propyl, isopropyl, butyl, isobutyl or tert-butyl group.

By (C$_2$–C$_6$) or respectively (C$_2$–C$_4$)alkylene (alk) is meant a linear or branched group.

By (C$_2$–C$_4$)alkenyl is meant a linear or branched C$_2$–C$_4$ unsaturated aliphatic group, preferably an allyl group.

When R$_8$ and R$_9$, together with the nitrogen atom to which they are connected, constitute a heterocyclic radical this radical is preferably selected from the following: azetidinyl, pyrrolidinyl, piperidinyl, perhydroazepinyl, piperazinyl, morpholino and thiomorpholino.

Since the compounds of formula (I) are oximes or oxime ethers they exist in two forms: syn and anti; the present invention embraces each of the two isomers and the mixture of these two isomers in any proportions.

When the compounds of formula (I) include a sulfur atom or an asymmetric carbon atom, all of the optical isomers, and a mixture thereof in any proportions, are provided by the invention.

The salts are generally prepared with pharmaceutically acceptable acids, though salts of other acids useful for purifying or isolating compounds of formula (I) also form part of the invention.

Preferentially the present invention relates to the compounds of formula (I) in which Ar, A, Y, R$_1$, R$_2$, R$_3$, R'$_3$, R$_4$, R$_5$, R$_6$ and R$_7$ are as defined above and R represents hydrogen or a (C$_1$–C$_4$)alkyl group.

The present invention most particularly provides compounds of formula (I) in which:

Ar represents:
   a) a phenyl which is mono-, di- or trisubstituted by one or more groups selected from the following: a halogen atom, a (C$_1$–C$_4$)alkyl, a trifluoromethyl, an amino, a nitro, a (C$_1$–C$_4$)alkoxy, a (C$_1$–C$_4$)alkylsulfanyl, a (C$_1$–C$_4$)alkylsulfonyl;
   b) a naphthyl which is unsubstituted or substituted once or twice by a halogen atom, a (C$_1$–C$_4$)alkyl group or a trifluoromethyl;

A represents a group (CH$_2$)$_n$ where n represents 2, 3 or 4;
Y represents a group selected from SR$_4$, SOR$_4$, SO$_2$R$_4$, SO$_2$NR$_5$R$_6$, N(R$_7$)SO$_2$R$_4$ and OR$_4$;
R represents hydrogen, a (C$_1$–C$_4$)alkyl or (C$_2$–C$_4$)alkenyl group or a group (C$_2$–C$_4$)alk-NR$_8$R$_9$;
R$_1$ is in position 7 of the indole ring system and represents a halogen atom or a (C$_1$–C$_4$)alkyl, trifluoromethyl or (C$_1$–C$_4$)alkoxy group;
R$_2$ represents hydrogen or a (C$_1$–C$_4$)alkyl group;
R$_3$ represents a hydrogen or halogen atom or a (C$_1$–C$_4$)alkyl group;
R'$_3$ is hydrogen;
R$_4$ represents a (C$_1$–C$_4$)alkyl group;
R$_5$ and R$_6$ represent each independently hydrogen or a (C$_1$–C$_4$)alkyl group;
R$_7$ represents hydrogen or a (C$_1$–C$_4$)alkyl group;

R$_8$ and R$_9$ represent a (C$_1$–C$_4$)alkyl or, together with the nitrogen atom to which are connected, constitute a heterocyclic radical selected from: azetidinyl, pyrrolidinyl, piperidinyl, perhydroazepinyl, piperazinyl, 4-methylpiperazin-1-yl, morpholino and thiomorpholino;

and their salts, where appropriate, and their solvates.

Preference is given to the compounds of formula (I) in which:

Ar represents a phenyl which is mono- or disubstituted by a halogen atom or a methyl, trifluoromethyl, methoxy, methylsulfanyl or methylsulfonyl group;
A represents a group (CH$_2$)$_n$ where n represents 2, 3 or 4;
Y represents a group SO$_2$R$_4$ or NHSO$_2$R$_4$;
R$_1$ represents a methyl group or a chlorine or bromine atom in position 7 of the indole ring system;
R$_2$ represents a methyl group;
R$_3$ is hydrogen or R$_3$ is in position 6 of the indole ring system and represents either a chlorine atom or a methyl group;
R'$_3$ is hydrogen;
R$_4$ represents a methyl or ethyl group;
R represents hydrogen, a methyl or ethyl group or a —(CH$_2$)$_3$N(CH$_3$)$_2$ moiety;

and their salts, where appropriate, and their solvates.

The present invention also provides a process for preparing compounds of formula (I), their salts, where appropriate, and their solvates.

This process is characterized in that an aroylindole derivative of formula:

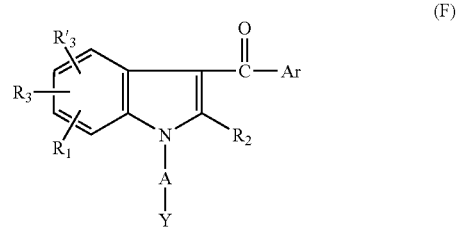

(F)

is treated with a hydroxylamine derivative of formula H$_2$NOR in which R is as defined above for (I).

The reaction is performed in a polar solvent such as ethanol or a pyridine/ethanol mixture at a temperature between the ambient temperature and the boiling temperature of the solvent.

Where appropriate the compound of formula (I) thus obtained is converted into one of its salts or solvates.

The compound obtained is isolated; generally it is composed of a mixture of the syn and anti isomers of the oxime or oxime ether according to the invention.

The separation of the syn and anti isomers may be performed using a process known to the skilled worker: for example, preparative chromatography.

According to one process of the present invention it is also possible to treat the compound of formula (F) with hydroxylamine (NH$_2$OH), according to the process described above, and, in a subsequent step, to treat the oxime thus obtained, of formula:

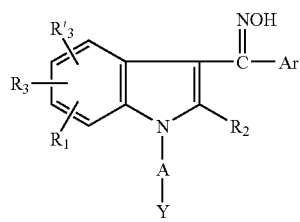

(Ia)

with an alkyl or alkenyl halide of formula RX, in which X represents a halogen atom, or with an alkyl or alkenyl sulfate of formula $(R)_2SO_4$.

The reaction is performed in the presence of a base such as sodium hydroxide, using a protic solvent such as ethanol, or in the presence of sodium hydride in an oxygen-containing solvent such as tetrahydrofuran at a temperature between the ambient temperature and the boiling temperature of the solvent.

The compounds of formula (F) can be prepared according to various processes, which are described below.

One process, called process A, comprises the following steps:
a) an indole of formula:

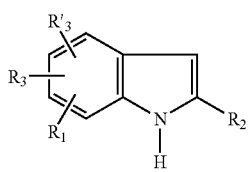

(II)

in which $R_1$, $R_2$, $R_3$ and $R'_3$ are as defined for a compound of formula (I) is treated with a methylmagnesium halide and with an acid halide of formula ArCOHal (III), in which Ar is as defined for the compound of formula (I) and Hal represents a halogen atom, preferably chlorine;
b) the compound thus obtained, of formula:

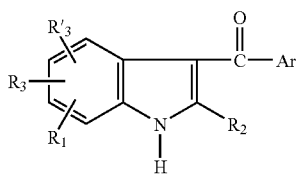

(IV)

is treated with a halide of formula Hal-A-Y (V), in which -A- and Y are as defined for a compound of formula (I) and Hal represents a halogen atom, preferably bromine, in the presence of a base.

In step a) of the above process the acylation is performed in a solvent such as ether.

Step b) is carried out in the presence of a base such as sodium carbonate or potassium carbonate, a hydride such as sodium hydride or an alkali metal hydroxide such as potassium hydroxide; and in a solvent such as toluene, DMSO or DMF, at a temperature between the ambient temperature and the boiling temperature of the solvent. In particular, when the base used is an alkali metal hydroxide, it is also possible to perform step b) in the presence of tris[2-(2-methoxyethoxy)-ethyl]amine (TDA-1), as described in Tetrahedron Lett., 1987, 28, 2963, or in the presence of a quaternary ammonium salt, such as tetrabutylammonium hydrogensulfate.

There exists a variant of process A, called process $A_1$, in which step b) of process A is modified as follows:
b1) the compound obtained in step a), of formula:

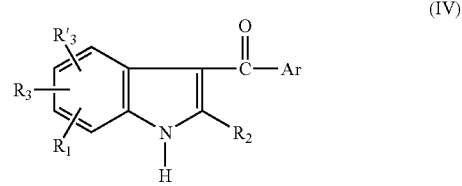

(IV)

is treated with a compound of formula Z-A-Cl (VI) in which Z represents either a hydroxyl group or a halogen atom, preferably bromine, and -A- is as defined for (I);
b2) optionally the compound thus obtained, of formula:

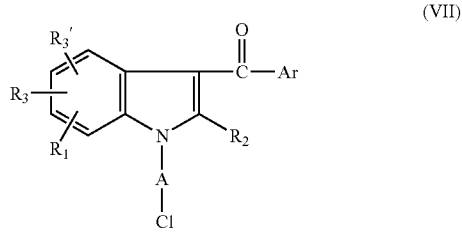

(VII)

is treated with sodium iodide;
b3) the compound thus obtained in step b1), of formula (VII), or in step b2), of formula:

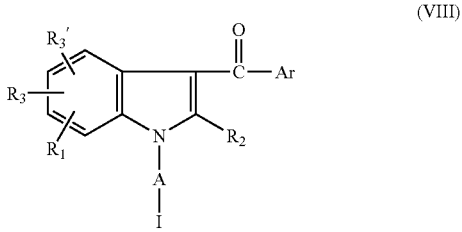

(VIII)

is treated with an anion $Y^\ominus$, Y being as defined for a compound of formula (I), to give the compound of formula (I).

When Z represents a halogen atom step b1) is performed in the presence of a base; when Z represents a hydroxyl group step b1) is performed in the presence of triphenylphosphine and diethyl azodicarboxylate in a solvent such as dichloromethane.

In step b2), when it is carried out, a solvent such as acetonitrile, acetone or another ketonic solvent is used.

To perform step b3) an anion is used which is obtained by reacting a compound of formula YH(IX) with NaH in a solvent such as DMF.

Process $A_1$ is particularly preferred for preparing compounds of formula (I) in which Y represents $SR_4$ or $NHSO_2R_4$.

According to another variant of process A, called process $A_2$, a compound of formula (I) in which Y represents a group $SOR_4$ or a group $SO_2R_4$ can be prepared from a compound of formula (I) in which Y represents a group $SR_4$. According to this process, after step b) of process A or step b2) or b3) of process $A_1$, the following additional step is performed:

c1) the compound obtained, of formula:

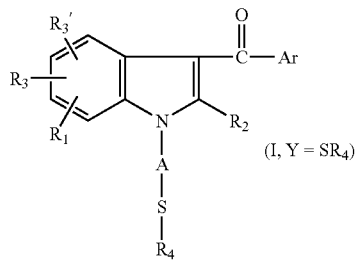

(I, Y = $SR_4$)

is treated with an oxidizing agent.

As oxidizing agent it is possible to use hydrogen peroxide or 3-chloroperbenzoic acid; depending on the number of equivalents of oxidizing agent used and on the temperature of the reaction, a sulfoxide (I, Y=$SOR_4$) or a sulfone (I, Y=$SO_2R_4$) is obtained.

According to another variant of process A, called process $A_3$, a compound of formula (I) in which Y represents a group $N(R_7)SO_2R_4$, in which $R_7$ is other than H, can be prepared from a compound of formula (I) in which Y represents a group $NHSO_2R_4$. According to this process, after step b) of process A or step b2) or b3) of process $A_1$ the following additional step is performed:

c2) the compound obtained, of formula:

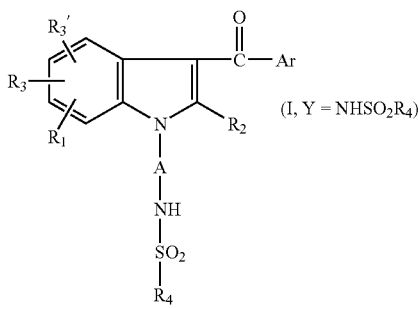

(I, Y = $NHSO_2R_4$)

is treated with an alkylating agent in the presence of a base.

As alkylating agent use is made, for example, of a dialkyl sulfate of formula $SO_4(R_7)_2$ or an alkyl halide of formula $R_7Hal$, $R_7$ in these formulae being as defined for the compounds of formula (I) and Hal representing a halogen atom, preferably iodine, in the presence of a base, such as sodium hydride for example.

According to yet another variant of process A, called process $A_4$, a compound of formula (I) in which Y represents a group $SO_2NR_5R_6$ can be prepared from a compound of formula (I) in which Y represents a group $SO_2NHR_5$. According to this process, after step b) of process A or step b2) or b3) of process $A_1$, the following additional step is performed:

c3) the compound obtained, of formula:

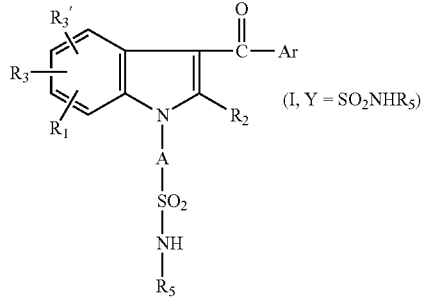

(I, Y = $SO_2NHR_5$)

is treated with an alkylating agent in the presence of a base.

As alkylating agent use is made, for example, of a dialkyl sulfate of formula $SO_4(R_6)_2$ or an alkyl halide of formula $R_6Hal$, $R_6$ in these formulae being as defined for the compounds of formula (I) and Hal representing a halogen atom, preferably iodine, in the presence of a base such as sodium hydride.

When it is desired to prepare a compound according to the invention of formula (I) in which Y represents a group $NR_7SO_2R_4$ or a group $NR_7SO_2NR_5R_6$ it is possible to use a variant of process A called process $A_5$. According to this process:

b4) the compound obtained in step b1), of formula:

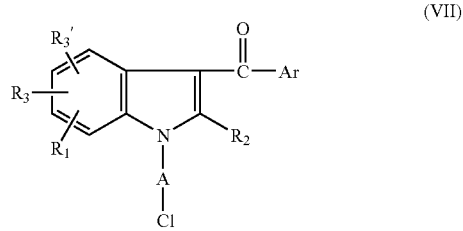

(VII)

is converted into a compound of formula:

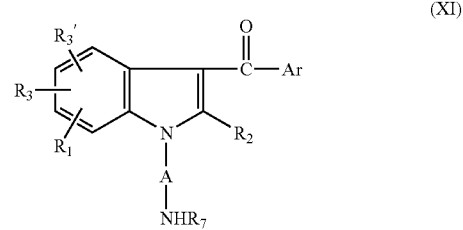

(XI)

in which $R_7$ is as defined for (I);

c4) it is treated with a halide of formula $HalSO_2R_4$ or respectively $HalSO_2NR_5R_6$, in which $R_4$, $R_5$ and $R_6$ have the meanings given above for (I).

Step b4) may be carried out by various processes known to the skilled worker: for example, the Delepine reaction (Synthesis, 1979, pp. 161–179), the Gabriel reaction (Angew. Chem. Int. Ed. Engl., 1998, 7, 919–930) or the reaction of Hebrard (Bull. Soc. Chim. Fr., 1970, 1938).

Step c4) can be carried out in the presence of a base such as triethylamine.

According to one alternative method of process A described above and of its variants, the alkylation of the indole nitrogen can be performed first of all and then the acylation of the compound thus obtained can be performed. In accordance with this alternative process, called process B:

i) an indole of formula:

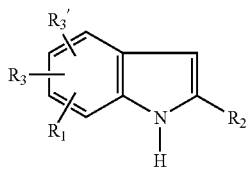

(II)

in which $R_1$, $R_2$, $R_3$ and $R'_3$ are as defined for the compound of formula (I) is treated with a halide of formula Hal-A-Y (V), in which -A- and Y are as defined for a compound of formula (I) and Hal represents a halogen atom, preferably bromine, in the presence of a base;

ii) the compound thus obtained, of formula:

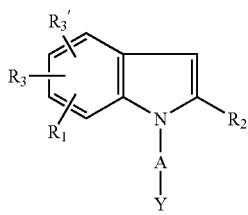

(XII)

is treated with an acid halide of formula ArCOHal (III) in which Ar is as defined for the compound of formula (I) and Hal is a halogen atom, preferably chlorine or bromine.

Step i) of the above process is carried out under the conditions described for step b) of process A. Step ii) is carried out under Friedel-Crafts conditions in the presence of a Lewis acid such as $AlCl_3$ or ethylaluminum dichloride in an inert solvent such as dichloromethane or dichloroethane, in accordance with the process described in J. Med. Chem., 1995, 38, 3094.

A variety of variants of step i) of process B exist. These variants correspond to what was described for process A.

According to variant $B_1$ of process B:

i1) an indole of formula:

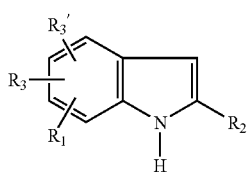

(II)

in which $R_1$, $R_2$, $R_3$ are as defined for the compound of formula (I) is treated with a compound of formula Z-A-Cl (VI) in which -A- is as defined for the compound of formula (I) and Z represents a hydroxyl group or a halogen atom, preferably bromine;

i2) where appropriate the compound thus obtained, of formula:

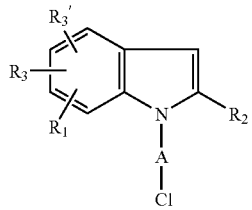

(XIII)

is treated with sodium iodide;

i3) the compound thus obtained in step i1) or in step i2), of formula:

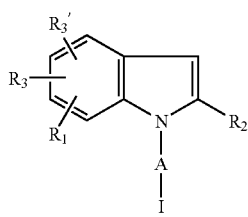

(XIV)

is treated with an anion of formula $Y^-$, Y being as defined for a compound of formula (I);

ii) the compound thus obtained, of formula:

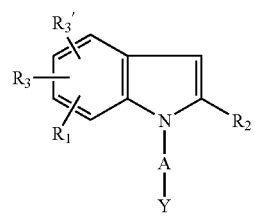

(XII)

is treated with an acid halide of formula ArCOHal (III) in which Ar is as defined for the compound of formula (I) and Hal is a halogen atom, preferably chlorine.

In particular, when it is desired to prepare a compound of formula (I) in which A is $(CH_2)_2$, it is possible to use techniques which are known to the skilled worker in order to introduce the alkyl chain of appropriate length in one of the steps, either of method A or of method B.

The indoles of formula (II) are known or are prepared by known methods as described in J. Am. Chem. Soc., 1974, 96, 5495 and 1974, 96, 5512 or in Tetrahedron Lett., 1989, 30, 2129.

The compounds according to the invention have shown a good in vitro affinity for ($CB_2$) cannabinoid receptors and a markedly weaker in vitro affinity for ($CB_1$) cannabinoid receptors, whether human receptors or rodent receptors. Affinity binding assays were carried out according to the experimental conditions described by Devane et al. (Molecular Pharmacology, 1988, 34, 605–613), with membranes obtained from cell lines in which the $CB_1$ receptors (Matsuda et al., Nature 1990, 346, 561–564) and $CB_2$ receptors (Munro et al., Nature 1993, 365, 61–65) were expressed. For human receptors the in vitro affinity for $CB_2$ cannabinoids, expressed in the form of the Ki (inhibition constant), is of the order of nM and the ratio of the affinity for $CB_1$ receptors to that for $CB_2$ receptors is at least 100.

The agonist or antagonist nature of the compounds according to the invention was demonstrated by the results obtained in models of the inhibition of adenylate cyclase as described in M. Rinaldi-Carmona et al., J. Pharmacol. Exp. Ther. 1996, 278, 871–878 and 1998, 284, 644–650.

The compounds according to the invention likewise possess an in vivo affinity for the cannabinoid receptors present in mouse spleen when they are administered orally. The tests were carried out according to the experimental conditions described by Rinaldi-Carmona et al., J. Pharmacol. Exp. Ther., 1998, 284, 644–650.

The compounds of the present invention are, in particular, active principles for pharmaceutical compositions whose toxicity is compatible with their use as medicinal products.

According to one of its aspects the present invention relates to the use of a compound of formula (I) or of one of its pharmaceutically acceptable salts or solvates for preparing medicinal products intended for preventing or treating any pathology in which $CB_2$ cannabinoid receptors are involved.

Mention may be made, for example, of the following diseases or conditions: immune system disorders, particularly autoimmune diseases: psoriasis, lupus erythematosus, connective tissue diseases, Sjogrer's syndrome, ankylosing spondylarthritis, rheumatoid arthritis, reactional arthritis, indifferentiated spondylarthritis, Behcet's disease, autoimmune hemolytic anemias, multiple sclerosis, amyotrophic lateral sclerosis, amyloses, graft rejection, diseases affecting the plasma cell line; allergic diseases: delayed or immediate hypersensitivity, allergic rhinitis, contact dermatitis, allergic conjunctivitis; infectious parasitic, viral or bacterial diseases: AIDS or meningitis; amylosis, diseases affecting the lines of the lymphohematopoietic system; inflammatory diseases, particularly diseases of the joints: arthritis, rheumatoid arthritis, osteoarthritis, spondylitis, gout, vasculitis, Crohn's disease, inflammatory bowel disease or irritable bowel syndrome (IBD or IBS), pancreatitis; osteoporosis; pain: chronic inflammatory pain, neuropathic pain, acute peripheral pain; eye conditions: ocular hypertension, glaucoma; pulmonary conditions: diseases of the respiratory tract, asthma, chronic bronchitis, chronic obstructive pulmonary disease (COPD), emphysema; diseases of the central nervous system and neurogenerative diseases: Tourette's syndrome, Parkinson's disease, Alzheimer's disease, senile dementia, chorea, Huntington's chorea, epilepsy, psychoses, depression, spinal cord lesions; migraine, vertigo, vomiting, nausea, in particular that following chemotherapy; cardiovascular diseases, in particular hypertension, arteriosclerosis, heart attack, cardiac ischemia; renal ischemia; cancers: benign skin tumors, papillomas and cancerous tumors, tumors of the prostate, cerebral tumors (glioblastomas, medulloepitheliomas, medulloblastomas, neuroblastomas, neuroblastomas, tumors of embryonic origin, astrocytomas, astroblastomas, ependymomas, oligodendrogliomas, plexus tumor, neuroepitheliomas, epiphyseal tumor, ependymoblastomas, neuroectodermic, malignant meningiomas, sarcomatoses, malignant melanomas, schwannomas); gastrointestinal diseases; obesity; and diabetes.

The use of the compounds according to the invention for preventing and/or treating the abovementioned diseases and also for preparing medicinal products intended for treating these diseases forms an integral part of the invention.

The compounds of formula (I) above, or one of their pharmaceutically acceptable salts or solvates, can be used at daily doses of from 0.01 to 100 mg per kilo of body weight of the mammal to be treated, preferably at daily doses of from 0.1 to 50 mg/kg. In humans the dose can vary preferably from 0.01 to 4000 mg per day, more particularly from 0.5 to 1000 mg, depending on the age of the subject to be treated or on the type of treatment, i.e., prophylactic or curative.

Thus according to another of its aspects the present invention provides pharmaceutical compositions comprising as active principle a compound of formula (I) or one of its pharmaceutically acceptable salts or solvates and also one or more pharmaceutically acceptable excipients.

In the pharmaceutical compositions of the present invention for oral, sublingual, inhaled, subcutaneous, intramuscular, intravenous, topical, local, intratracheal, intranasal, transdermal, local or rectal administration, the active principles may be administered in unit administration forms, in a mixture with conventional pharmaceutical vehicles, to animals and to human beings.

The appropriate unit administration forms include oral forms such as tablets, soft or hard gel capsules, powders, granules, oral solutions or suspensions, sublingual, buccal, intratracheal, intraocular, intranasal and inhalation administration forms, aerosols, topical and transdermal administration forms, implants, subcutaneous, intramuscular and intravenous administration forms and rectal administration forms.

For topical administration the compounds according to the invention can be used in creams, ointments, gels or lotions.

In each dosage unit the active principle of formula (I) is present in the amounts appropriate for the daily dosages envisaged. Generally each dosage unit is suitably adjusted according to the dosage and the type of administration contemplated—for example, tablets, gel capsules and the like, sachets, ampoules, syrups and the like, and drops—such that one dosage unit of this kind contains from 0.1 to 1000 mg of active principle, preferably from 0.5 to 250 mg, which must be administered one to four times per day.

Although these dosages are examples of average situations there may be specific cases in which higher or lower dosages are appropriate, and such dosages also belong to the invention. In accordance with customary practice the dosage appropriate for each patient is determined by the doctor in accordance with the method of administration and the age, weight and response of said patient.

It will also be possible to use the compounds according to the invention for preparing compositions for veterinary use.

Furthermore, the compounds according to the invention, as they are or in radiolabeled form, can be used as pharmacological tools in humans or animals, for the detection and labeling of $CB_2$ cannabinoid receptors.

The following Preparations and Examples illustrate the invention, though without limiting it.

In the Preparations and in the Examples the following abbreviations are used:

ether: diethyl ether iso ether: diisopropyl ether

DMF: N,N-dimethylformamide

THF: tetrahydrofuran

DCM: dichloromethane

AcOEt: ethyl acetate

TDA-1: tris[2-(2-methoxyethoxy)ethyl]amine hydrochloric ether: saturated solution of hydrochloric acid in diethyl ether Triton B: N-benzyltrimethylammonium hydroxide m.p.: melting point AT: ambient temperature b.p.: boiling temperature The proton magnetic resonance ($^1$H NMR) spectra are recorded at 200 MHz in DMSO-$d_6$, using the DMSO-$d_6$ peak as reference. The chemical shifts δ are expressed in parts per million (ppm). The signals observed are expressed thus: s: singlet; bs: broad singlet; d: doublet; dd: double doublet; t: triplet; dt: double triplet; bt: broad triplet; q: quartet; bq: broad quartet; qt: quintet; m: unresolved multiplet; mt: multiplet; sp: septet.

Preparation of indoles of formula (II).

Preparation 1.1

2-Methyl-7-chloro-1H-indole.

Under a nitrogen atmosphere 42.1 g of 2-chloronitrobenzene are placed in 850 ml of THF. The mixture is cooled to −40° C. and then 1.6 l of isopropenylmagnesium bromide at 0.5 M in THF are added dropwise. After 1 hour at −40° C. with stirring the mixture is hydrolyzed with 400 ml of saturated NH$_4$Cl solution. The aqueous phase is extracted twice with ether. The organic phase is dried and then evaporated and the residue is chromatographed on silica, eluting with toluene. This gives 20.3 g of the expected compound.

NMR: δ (ppm): 2.4: s: 3H; 6.2: s: 1H; 6.9: t: 1H; 7.1: d: 1H; 7.4: d: 1H; 11.2: bs: 1H.

Preparation 1.2

7-Bromo-2-methyl-1H-indole.

27.0 g of 2-bromonitrobenzene are placed in 400 ml of THF. The mixture is placed under nitrogen and cooled to −55° C. and then 800 ml of isopropenylmagnesium bromide at 0.5 M in THF are added dropwise. The mixture is left with stirring for 1 hour and then poured into saturated NH$_4$Cl solution. It is extracted with ether, the extract is evaporated and then the residue is taken up in DCM. It is washed with saturated NaCl solution. It is dried and evaporated and then the residue is chromatographed on silica, eluting with an AcOEt/cyclohexane (1/9; v/v) mixture. This gives 10.7 g of the expected compound.

NMR: δ (ppm): 2.4: s: 3H; 6.2: s: 1H; 6.9: t: 1H; 7.2: d: 1H; 7.4: d: 1H; 11.2: bs: 1H.

Preparation 1.3

6,7-Dichloro-2-methyl-1H-indole.

1600 ml of isopropenylmagnesium bromide at 0.5 M in THF are introduced under nitrogen and cooled to −20° C., 51.2 g of 2,3-dichloronitrobenzene in 250 ml of anhydrous THF are added and then the mixture is left with stirring at −20° C. for 1 hour. The reaction mixture is poured at −20° C. into 1 liter of saturated NH$_4$Cl solution and diluted with Et$_2$O and then the aqueous phase is washed twice with Et$_2$O. The organic phases are combined and concentrated to dryness. The product is extracted with DCM and washed twice with water and then with saturated NaCl solution. It is dried and then evaporated and the residue is chromatographed on a hexane/AcOEt (95/5; v/v) mixture. This gives 24.27 g of the expected compound, m.p.=70–71° C.

In this way the indole derivatives described in table 1 below were prepared:

TABLE 1

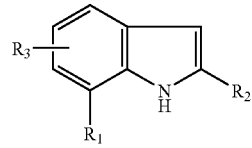

| Preparations | $R_1$ | $R_2$ | $R_3$ | m.p. ° C./NMR: δ (ppm) |
|---|---|---|---|---|
| 1.1 | Cl | Me | H | NMR |
| 1.2 | Br | Me | H | NMR |
| 1.3 | Cl | Me | 6-Cl | 70–71° C. |
| 1.4 | Cl | Me | 5-Cl | 56° C. |
| 1.5 | Cl | Me | 6-Me | 2.35: s: 3H; 3.85: s: 3H; 6.15: s: 1H; 6.85: d: 1H; 7.15: d: 1H; 11.20: s: 1H |
| 1.6 | F | Me | H | 2.40: s: 3H; 6.20: mt: 1H; 6.70–7.30: m: 3H; 11.30: s: 1H |
| 1.7 | Cl | Et | H | 1.30: t: 3H; 2.80: q: 2H; 6.25: s: 1H; 6.80–7.60: m: 3H; 11.20: bs: 1H |

Process A is used to prepare the intermediates of formula (IV) described below:

TABLE 2

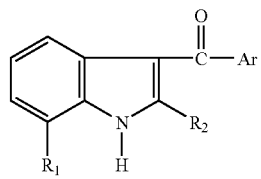

(IV)

| Preparations | $R_1$ | $R_2$ | Ar | m.p. ° C./NMR: δ (ppm) |
|---|---|---|---|---|
| 2.1 | Cl | Me | 2,3-dichlorophenyl | 2.2: s: 3H; 7: t: 1H; 7.1 to 7.5: m: 4H; 7.7: d: 1H; 12.3: bs: 1H |
| 2.2 | Cl | Me | 2-F,3-CF$_3$-phenyl | 2.4: s: 3H; 7.2: t: 1H; 7.3: d: 1H; 7.4: d: 1H; 7.7: mt: 2H; 7.9: t: 1H; 8: t: 1H; 12.6: s: 1H |
| 2.3 | Cl | Me | 2-Br,3-Me-phenyl | 2.2: s: 3H; 2.4: s: 3H; 7.0: t: 1H; 7.2: m: 2H; 7.3 to 7.6: m: 3H |
| 2.4 | Br | Me | 2,3-dichlorophenyl | 2.4: s: 3H; 7.0: t: 1H; 7.5: mt: 3H; 7.6: t: 1H; 7.9: dd: 1H; 12.3: s: 1H |
| 2.5 | OMe | Me | 1-(4-bromonaphthyl) | 120° C. |

Process B or process B₁ is used to prepare the intermediates of formula (XII) described below:

TABLE 3

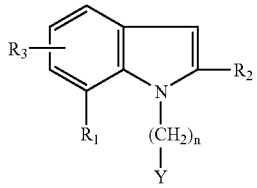
(XII)

| Pre-parations | R₁ | R₂ | R₃ | n | Y | NMR/ m.p. ° C. | Process |
|---|---|---|---|---|---|---|---|
| 3.1 | Cl | Me | H | 2 | SEt | NMR | B |
| 3.2 | Cl | Me | H | 3 | NHSO₂Me | NMR | B₁ |
| 3.3 | Br | Me | H | 3 | NHSO₂Me | NMR | B₁ |
| 3.4 | Cl | Et | H | 3 | NHSO₂Me | 98° C. | B₁ |
| 3.5 | Cl | Me | 6-Cl | 3 | NHSO₂Me | NMR | B₁ |
| 3.6 | Cl | Me | 6-Me | 3 | NHSO₂Me | NMR | B₁ |
| 3.7 | Cl | Me | H | 3 | NHSO₂NMe₂ | 81° C. | B₁ |
| 3.8 | H | Me | H | 3 | NHSO₂Me | NMR | B₁ |

Preparation 3.1: NMR: δ (ppm): 1.25: t: 3H; 2.4 to 2.8: m: 5H; 3: t: 2H; 4.8: t: 2H; 7 to 8.2: m: 6H.

Preparation 3.2: NMR: δ (ppm): 1.8: qt: 2H; 2.4: s: 3H; 2.9: s: 3H; 3.0: t: 2H; 4.4: t: 2H; 6.2: s: 1H; 6.9: t: 1H; 7: mt: 2H; 7.4: dd: 1H.

Preparation 3.3: NMR: δ (ppm): 1.8: mt: 2H; 2.4: s: 3H; 2.8: s: 3H; 3.0: qt: 2H; 4.4: t: 2H; 6.2: s: 1H; 6.8: t: 1H; 7.0: t: 1H; 7.2 and 7.4: dd: 2H.

Preparation 3.5: NMR: δ (ppm): 1.85: qt: 2H; 2.40: s: 3H; 2.90: s: 3H; 3: q: 2H; 4.5: t: 2H; 6.3: s: 1H; 7 to 7.5: m: 3H.

Preparation 3.6: NMR: δ (ppm): 1.85: qt: 2H; 2.40: s: 6H; 2.90: s: 3H; 3: q: 2H; 4.5: t: 2H; 6.3: s: 1H; 7 to 7.5: m: 3H.

Preparation 3.8: NMR: δ (ppm): 1.85: qt: 2H; 2.40: s: 3H; 2.90: s: 3H; 3.0: q: 2H; 4.15: t: 2H; 6.20: s: 1H; 7 to 7.60: m: 5H.

Preparation 4.1 (Process B₁)
N-(3-(7-Chloro-3-(2-fluoro-3-trifluoromethylphenyl)-2-methyl-1H-indol-1-yl)propyl)methanesulfonamide.

(F): R₁=Cl, R₂=Me, R₃=R'₃=H, Ar=2-fluoro-3-trifluoromethylphenyl, Y=NHSO₂Me, A=(CH₂)ₙ, n=3.

A) 7-Chloro-1-chloropropyl-2-methyl-1H-indole.

Under nitrogen 40 g of 7-chloro-2-methyl-1H-indole are placed in 60 ml of toluene with 2.8 g of KOH. After 30 minutes with stirring at AT, 7.7 g of 3-chloro-1-bromopropane are added and then the mixture is heated at reflux for 3 hours. The mixture is extracted with ether. The organic phase is washed with water, with 10% HCl solution, with water and with saturated NaCl solution. It is dried and evaporated to give 6.19 g of the expected compound.

B) N-(3-(7-Chloro-2-methyl-1H-indol-1-yl)propyl)methanesulfonamide.

Under nitrogen a mixture is prepared containing 2.2 g of NaH at 60% in oil and 170 ml of DMF, and this mixture is cooled to 0° C. 4.0 g of NH₂SO₂CH₃ are added and then the mixture is allowed to return to AT and 5.0 g of the compound from the preceding step are added. The mixture is heated at 130° C. for 6 hours. It is extracted with DCM and the organic phase is washed with water and then with saturated NaCl solution. It is dried and evaporated and then the residue is chromatographed on silica, eluting with a cyclohexane/AcOEt (30/70; v/v) mixture. This gives 1.92 g of the expected compound.

C) N-(3-(7-Chloro-3-(2-fluoro-3-trifluoromethylphenyl)-2-methyl-1H-indol-1-yl)propyl)methanesulfonamide.

Under nitrogen 0.80 g of the compound from the preceding step and 0.90 g of 2-fluoro-3-trifluoromethylbenzoyl chloride are mixed in 60 ml of DCM. The temperature is lowered to 0° C. and then 34 ml of dichloroethylaluminum at 1.8 M in toluene are added. The mixture is allowed to return to AT and is then stirred for 15 hours. It is extracted with DCM. The organic phase is washed with water and with saturated NaCl solution. It is dried and evaporated. The product is recrystallized from a DCM/ether mixture. This gives 550 mg of the expected compound, m.p.=168° C.

NMR: δ (ppm): 2: mt: 2H; 2.4: s: 3H; 3.0: s: 3H; 3.2: mt: 2H; 4.7: mt: 2H; 7 to 7.5: m: 3H; 7.7: t: 1H; 8: t: 1H; 8.2: t: 1H.

Preparation 4.2
7-Bromo-2-methyl-1-(3-methylsulfinyl)propyl)-1H-indol-3-yl)-2,3-dichlorophenyl)methanone.

(F): R₁=Br, R₂=Me, R₃=R'₃=H, Ar=2,3-dichlorophenyl, Y=-SOMe, A=(CH₂)ₙ, n=3.

A) (7-Bromo-2-methyl-1H-indol-3-yl)(2,3-dichlorophenylmethanone).

10.7 g of 7-bromo-2-methyl-1H-indole are placed in 100 ml of THF and cooled to −10° C. At this temperature 22 ml of methylmagnesium bromide at 3M in ether are added. The mixture is allowed to return to AT and then cooled to −5° C. and 13.5 g of 2,3-dichlorobenzoyl chloride in solution in 80 ml of THF are added dropwise. The mixture is allowed to return to AT and then poured into saturated NH₄Cl solution. It is extracted with ether and then the organic phase is washed with 10% NaOH solution, water and saturated NaCl solution. It is dried and evaporated and the residue is chromatographed on silica, eluting with an AcOEt/cyclohexane (10/90; v/v) mixture. The resulting product crystallizes from ether to give 5 g of the expected compound.

B) (7-Bromo-2-methyl-1-(3-chloropropyl)-1H-indol-3-yl)(2,3-dichlorophenyl)methanone. 1 g of crushed potassium hydroxide is admixed with 3 g of the compound from the preceding step, 0.3 g of TDA-1 and 100 ml of toluene and then the mixture is heated at reflux for 30 minutes and 5 g of 1-bromo-3-chloropropane are added. The mixture is allowed to cool to AT and then poured into 100 ml of 10% HCl solution. The mixture is extracted with toluene and then the organic phase is washed with water and then with saturated NaCl solution. It is dried and evaporated and the residue is then chromatographed on silica, eluting with DCM. This gives 3.25 g of the expected compound, m.p.=139° C.

C) (7-Bromo-2-methyl-1-(3-(methylsulfanyl)-propyl)-1H-indol-3-yl)(2,3-dichlorophenylmethanone)

At AT 3 g of the compound from the preceding step and 0.62 g of MeSNa are mixed in 40 ml of ethanol. The mixture is heated at reflux for 2 and a half hours and then allowed to cool. The mixture is poured into 10% sodium hydroxide solution. The mixture is extracted with ether and then the organic phase is washed with saturated NaCl solution. This gives 2 g of the expected compound, m.p.=119° C.

NMR: δ (ppm): 2: mt: 2H; 2.1: s: 3H; 2.4: s: 3H; 2.6: t: 2H; 4.6: t: 2H; 7: t: 1H; 7.4 to 7.6: m: 4H; 7.8: dd: 1H.

D) 7-Bromo-2-methyl-1-(3-(methylsulfinyl)-propyl)-1H-indol-3-yl)(2,3-dichlorophenyl)methanone.

2.5 g of the compound from the preceding step are placed in 50 ml of acetic acid and cooled to 10° C. 0.8 ml of H₂O₂ is added with stirring and then the mixture is allowed to return to AT and stirring is continued for 1 and a half hours. The mixture is evaporated and then extracted with AcOEt. The organic phase is washed with 10% NaOH solution, water and saturated NaCl solution. It is evaporated and the resulting product is recrystallized from an AcOEt/MeOH (9/1; v/v) mixture. This gives 1.1 g of the expected compound, m.p. 137° C.

NMR: δ (ppm): 2.1: qt: 2H; 2.4 and 2.6: 2s: 6H; 2.8 to 3.2: mt: 2H; 4.8: t: 2H; 7.1: t: 1H; 7.5: m: 4H; 7.9: d: 1H.

Preparation 4.3 (process B)

N-(3-(6,7-Dichloro-3-[2-fluoro-3-(trifluoromethyl)benzyl]-2-methyl-1H-indol-1-yl)propyl)methanesulfonamide.

(F): $R_1=R_3=Cl$, $R_2=Me$, $R'_3=H$, Ar=2F-3-$CF_3$-phenyl, Y=-$NHSO_2Me$, A=

A) 6,7-Dichloro-1-(3-chloropropyl)-2-methyl-1H-indole.

Under nitrogen 7.84 g of crushed sodium hydroxide, 190 ml of toluene, 7 g of 6,7-dichloro-2-methyl-1H-indole, 85 ml of toluene and 0.7 g of tetrabutylammonium hydrogensulfate are introduced. The mixture is heated at reflux for 30 minutes and then 14 ml of 1-bromo-3-chloropropane are added and the reflux is maintained for 2 hours. The reaction mixture is poured into water and the aqueous phase is washed with toluene. It is extracted with toluene and then washed with water and with saturated NaCl solution. It is dried and evaporated to give 11.3 g of the expected compound.

B) 6,7-Dichloro-1-(3-iodopropyl)-2-methyl-1H-indole.

11.3 g of the compound from the preceding step are introduced into 520 ml of acetonitrile and 43 g of NaI and then heated at reflux for 3 days. The reaction mixture is poured into water and diluted with toluene and then the aqueous phase is washed twice with toluene. The organic phases are combined and then washed with water and then with saturated NaCl solution. They are dried and concentrated to give 13.93 g of the expected compound.

C) N-[3-(6,7-Dichloro-2-methyl-1H-indol-1-yl)propyl]methanesulfonamide.

Under nitrogen 6.04 g of NaH at 60% are introduced into 400 ml of anhydrous DMF. The mixture is cooled to 5° C. and then 14.35 g of methanesulfonamide in 200 ml of anhydrous DMF are added. After 10 minutes with stirring at 5° C., 13.9 g of the compound obtained in the preceding step in 200 ml of anhydrous DMF are added and the mixture is allowed to return to AT. After 3 hours with stirring the reaction mixture is poured into water and then diluted with DCM. The aqueous phase is washed 3 times with DCM and then the organic phases are combined. They are washed with water and with saturated NaCl solution. They are dried and concentrated and the residue is then chromatographed on silica, eluting with a cyclohexane/AcOEt (50/50; v/v) mixture. This gives 7.43 g of the expected compound.

NMR: δ (ppm): 1.80: mt: 2H; 2.35: s: 3H; 2.60: s: 6H; 2.90: mt: 2H; 4.40: t: 2H; 6.30: s: 1H; 7.10: d: 1H; 7.20: mt: 1H; 7.35: d: 1H.

D) N-(3-(6,7-Dichloro-3-[2-fluoro-3-(trifluoromethyl)benzoyl]-2-methyl-1H-indol-1-yl)propyl)methanesulfonamide.

1 g of the compound from the preceding step and 1.35 g of 2-fluoro-3-(trifluoromethyl)benzoyl chloride are introduced into 120 ml of DCM. The mixture is cooled to between −20° C. and −25° C. and, using a syringe, 3.3 ml of dichloroethylaluminum are added. The mixture is allowed to return to ambient temperature and stirring is continued for 3 hours. The reaction mixture is poured into water, the aqueous phase is washed 3 times with DCM and then the organic phases are combined and filtered over Célite®. The product is washed with 10% NaOH solution, water, 10% HCl solution and then saturated NaCl solution. This gives 0.94 g of the expected compound, which crystallizes from ether, m.p.=181° C.

Employing one of the processes described, the compounds of formula II assembled in the table below were prepared:

TABLE 4

(F)

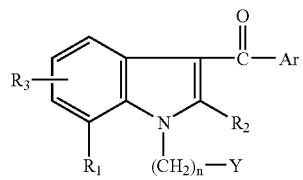

| Preparations | $R_1$ | $R_2$ | $R_3$ | n | Y | Ar | m.p. ° C./NMR | Process |
|---|---|---|---|---|---|---|---|---|
| 4.1 | Cl | Me | H | 3 | $NHSO_2Me$ | 2-F-3-$CF_3$-phenyl | NMR | $B_1$ |
| 4.2 | Br | Me | H | 3 | SOMe | 2,3-dichlorophenyl | NMR | $A_2$ |
| 4.3 | Cl |  | 6-Cl | 3 | $NHSO_2Me$ | 2-F-3-$CF_3$-phenyl | 181° C. | B |
| 4.4 | Cl | Me | H | 2 | $SO_2Et$ | 2-F-3-$CF_3$-phenyl | 187° C. | $A_2$ |
| 4.5 | Cl | Me | H | 3 | SOMe | 2,3-dichlorophenyl | NMR | $A_2$ |
| 4.6 | Br | Me | H | 3 | $NHSO_2Me$ | 2,3-dichlorophenyl | 147° C. | $A_1$ |
| 4.7 | Cl | Et | H | 3 | $NMeSO_2Me$ | 2-F-3-$CF_3$-phenyl | NMR | $A_3$ |
| 4.8 | Cl | Me | H | 3 | $NHSO_2Me$ | 2-Br-3-Me-phenyl | 75° C. | $B_1$ |
| 4.9 | H | Me | H | 3 | $NHSO_2Me$ | 2-F-3-$CF_3$-phenyl | 133° C. | $B_1$ |
| 4.10 | Cl | Me | 5-Cl | 3 | $NHSO_2Me$ | 2,3-dichlorophenyl | 86° C. | $B_1$ |
| 4.11 | Cl | Me | 6-Me | 3 | $NHSO_2Me$ | 2-F-3-$CF_3$-phenyl | 146° C. | $B_1$ |
| 4.12 | Cl | Me | H | 3 | $NHSO_2NMe_2$ | 2,3-dichlorophenyl | 110–113° C. | $B_1$ |
| 4.13 | Cl | Me | H | 3 | $NHSO_2NMe_2$ | 2-F-3-$CF_3$-phenyl | 158–160° C. | $B_1$ |
| 4.14 | F | Me | H | 3 | $NHSO_2Me$ | 2-F-3-$CF_3$-phenyl | 144–150° C. | $B_1$ |
| 4.15 | Br | Me | H | 3 | $NHSO_2Me$ | 2-F-3-Cl-phenyl | 191° C. | $B_1$ |
| 4.16 | Cl | Me | 6-Me | 3 | $NHSO_2Me$ | 2,4-dichlorophenyl | 117–120° C. | $B_1$ |
| 4.17 | OMe | Me | H | 3 | $NHSO_2Me$ | 1-(4-bromonaphthyl) | 72–77° C. | $A_5$ |

Preparation 4.5: NMR: δ (ppm): 2.1: mt: 2H; 2.4 to 2.6: 2s: 6H; 2.8: mt: 2H; 4.7: mt: 2H; 7.1: t: 1H; 7.2 to 7.6: m: 4H; 7.9: dd: 1H.

Preparation 4.7: NMR: δ (ppm): 1.15: t: 3H; 2.00: mt: 2H; 2.80: s: 3H; 2.85 to 3.10: m: 5H; 3.25: t: 2H; 4.55: t: 2H; 6.90 to 8.10: m: 6H.

EXAMPLE 1

Compound 1

(I): $R_1$=7-Cl, $R_2$=Me, $R_3$=$R'_3$=H, Ar=2-fluoro-3-trifluoromethylphenyl, Y=$SO_2Me$, A=$(CH_2)_3$, R=H.

N-(3-(7-Chloro-3-((2-fluoro-3-trifluoromethyl)phenyl)(hydroxyimino)methyl-2-methyl-1H-indol-1-yl)phenyl)methansulfonamide.

Under nitrogen 4.45 g of the compound from preparation 4.1 and 6.3 g of hydroxylamine are placed in a mixture of 25 ml of pyridine and 26 ml of ethanol and the mixture is heated at reflux overnight.

It is concentrated to dryness and then taken up in an ether/2N aqueous HCl solution mixture and the organic phase is washed with water (twice) and then with saturated NaCl solution.

It is dried over MgSO$_4$ and evaporated and then chromatographed on silica, eluting with a DCM/MeOH (100/1 to 97/3; v/v) mixture.

This gives 2.72 g of the expected compound, m.p.=172° C.

EXAMPLE 2

Compound 2

(I): $R_1$=7-Cl, $R_2$=Me, $R_3$=$R'_3$=H, Ar=2-fluoro-3-trifluoromethylphenyl, Y=SO$_2$Me, A=(CH$_2$)$_3$, R=Me.

N-(3-(7-Chloro-3-((2-fluoro-3-trifluoromethyl)phenyl)(methoxyimino)methyl-2-methyl-1H-indol-1-yl)propyl)methanesulfonamide.

Under nitrogen 1 g of the compound from preparation 4.1 and 1.70 g of O-methylhydroxylamine are placed in a mixture of 7.5 ml of pyridine and 11 ml of ethanol and heated at reflux for 3 days. The mixture is concentrated to dryness and the residue is then taken up in an ether/10% aqueous hydrochloric acid solution mixture.

The aqueous phase is washed twice with ether and the ethereal phases are combined and then washed with water and with saturated NaCl solution.

They are dried over MgSO$_4$ and then chromatographed on silica, eluting with a cyclohexane/AcOEt (50/50; v/v) mixture. This gives 1.06 g of the expected compound in the form of a glassy solid, m.p.=62–65° C.

EXAMPLE 3

Compound 28

N-(3-(7-Chloro-3-(((3-dimethylamino)propoxyimino)(fluoro-3-trifluoromethyl)phenyl)methyl)-2-methyl-1H-indol-1-yl)propyl)methanesulfonamide hydrochloride.

A) Acetone O-(3-(dimethylamino)propyl)oxime.

Under nitrogen, 1 litre of ethanol and then 46 g of sodium, cut into pieces, are introduced and cooled to 20° C. 73.1 g of acetooxime and 158 g of 3-chlorodimethylaminopropane hydrochloride are added and the mixture is heated at reflux for 2 hours. After overnight stirring at AT the NaCl formed is filtered off and then the mixture is acidified with 120 ml of concentrated HCl and concentrated to dryness. The residue is taken up in 100 ml of water and then at 10° C. 160 ml of concentrated sodium hydroxide solution are added. The mixture is extracted twice with ether and then dried over MgSO$_4$. The ether is distilled at atmospheric pressure and then the product is distilled under a pressure of 18 mm of mercury=2400 pascals. This gives 74.1 g of the expected compound.

B) 3-(aminooxy)propyldimethylamine dihydrochloride.

A mixture containing 74.1 g of the compound from the preceding step in 330 mg of water and 140 ml of concentrated HCl is heated at reflux overnight. The acetone formed is distilled off and reflux is continued for 1 hour. The mixture is concentrated to dryness, ethanol and toluene are added and then the mixture is concentrated to dryness again. The residue is taken up in 200 ml of isopropanol, and 200 ml of ether and then 200 ml of acetonitrile are added. After 1 hour with stirring the solid formed is filtered off and rinsed with acetonitrile containing 20% isopropanol and then with ether; it is dried under vacuum over P$_2$O$_5$ to give 75 g of the expected compound, m.p.=158° C.

C) N-(3-(7-Chloro-3-(((3-dimethylamino)propoxyimino)(fluoro-3-trifluoromethyl)phenyl)methyl)-2-methyl-1H-indol-1yl)propyl)methanesulfonamide hydrochloride.

Under nitrogen 0.79 g of the compound from preparation 4.1 and 3 g of 3-(aminooxy)propyldimethylamine dihydrochloride are placed in 40 ml of ethanol and the mixture is left with stirring at reflux for 6 hours. It is concentrated to dryness and the residue is then taken up in an ethyl acetate/2N aqueous HCl solution mixture. The organic phase is washed with saturated NaCl solution and then dried over MgSO$_4$ and evaporated. It is chromatographed on silica, eluting with a DMC/MeOH (95/5; v/v) mixture. This gives 280 mg of the expected compound, m.p.=68° C.

Working as described in the above examples, the compounds according to the invention collated in the table below are prepared.

The compounds are characterized by their melting point or their NMR spectrum; in every case it was verified that the NMR spectrum is compatible with the structure of the compound.

TABLE 5

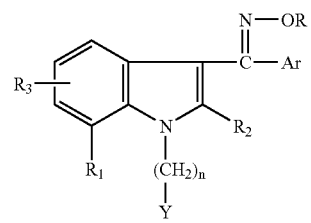

(I)

| Compounds | $R_1$ | $R_2$ | $R_3$ | n | Y | R | Ar | m.p. ° C./NMR |
|---|---|---|---|---|---|---|---|---|
| 1 | Cl | Me | H | 3 | SO$_2$Me | H | 2-F,3-CF$_3$-phenyl | 172° C. |
| 2 | Cl | Me | H | 3 | SO$_2$Me | Me | 2-F,3-CF$_3$-phenyl | 62–65° C. |

TABLE 5-continued (I)

Structure: Indole with substituent at 3-position being C(=N-OR)-Ar; R3 on benzene ring; R1 at 7-position; 2-position has R2; N-1 has (CH2)n-Y.

| Compounds | R₁ | R₂ | R₃ | n | Y | R | Ar | m.p. °C./ NMR |
|---|---|---|---|---|---|---|---|---|
| 3 | Cl | Me | H | 3 | SOMe | H | 2,3-dichlorophenyl | NMR |
| 4 | Cl | Et | H | 3 | N(Me)SO₂Me | H | 2-F,3-CF₃-phenyl | 130–148° C. |
| 5 | Cl | Me | 6-Me | 3 | NHSO₂Me | H | 2-F,3-CF₃-phenyl | 82–84° C. |
| 6 | Cl | Me | H | 3 | NHSO₂Me | H | 2-Br,3-Me-phenyl | 68–70° C. |
| 7 | Cl | Me | H | 2 | SO₂Et | H | 2-F,3-CF₃-phenyl | NMR |
| 8 | Cl | Me | H | 3 | NHSO₂Me | Et | 2-F,3-CF₃-phenyl | NMR |
| 9 | H | Me | H | 3 | NHSO₂Me | Me | 2-F,3-CF₃-phenyl | NMR |
| 10 | Br | Me | H | 3 | NHSO₂Me | Me | 2-F,3-Cl-phenyl | 49° C. |
| 11 | Cl | Me | H | 3 | NHSO₂NMe₂ | H | 2-F,3-CF₃-phenyl | 146–152° C. |
| 12 | Cl | Me | 5-Cl | 3 | NHSO₂Me | H | 2,3-dichlorophenyl | 68–73° C. |
| 13 | Cl | Me | 6-Me | 3 | NHSO₂Me | H | 2,4-dichlorophenyl | 185–187° C. |
| 14 | Cl | Me | 6-Me | 3 | NHSO₂Me | Me | 2,4-dichlorophenyl | 68–70° C. |
| 15 | Cl | Me | 6-Me | 3 | NHSO₂Me | Et | 2,4-dichlorophenyl | 62–66° C. |
| 16 | Br | Me | H | 3 | SOMe | Me | 2,3-dichlorophenyl | NMR |
| 17 | F | Me | H | 3 | NHSO₂Me | Me | 2-F,3-CF₃-phenyl | NMR |
| 18 | OMe | Me | H | 3 | NHSO₂Me | H | 1-(4-bromonaphthyl) | 167–170° C. |
| 19 | Cl | Me | H | 3 | NHSO₂NMe₂ | H | 2,3-dichlorophenyl | NMR |
| 20 | Cl | Me | H | 3 | NHSO₂NMe₂ | Me | 2,3-dichlorophenyl | 53–57° C. |
| 21 | Cl | Me | H | 3 | NHSO₂NMe₂ | Et | 2,3-dichlorophenyl | NMR |
| 22 | Cl | Me | H | 3 | NHSO₂NMe₂ | allyl | 2,3-dichlorophenyl | NMR |
| 23 | Cl | Me | 6-Cl | 3 | NHSO₂NMe | Me | 2-F,3-CF₃-phenyl | 148–150° C. |
| 24 | Br | Me | H | 3 | NHSO₂Me | Me | 2,3-dichlorophenyl | 65° C. |
| 25 | Br | Me | H | 3 | NHSO₂Me | allyl | 2-F,3-Cl-phenyl | 101° C. |
| 26 | Br | Me | H | 3 | SOMe | H | 2,3-dichlorophenyl | 63° C. |
| 27 | Cl | Me | Cl | 3 | NHSO₂Et | Me | 4-bromonaphthyl | 82-86° C. |
| 28 | Cl | Me | H | 3 | NHSO₂Me | —(CH₂)₃—NMe₂ | 2-F,3-CF₃-phenyl | 158° C. |

EXAMPLE 3

NMR: δ (ppm): 1.90 to 2.30: m: 5H; 2.56: s: 3H; 2.60 to 2.90: m: 2H; 4.61: dd: 2H; 6.80 to 7.70: m: 6H; 11.00 to 11.70: m: 1H.

EXAMPLE 7

NMR: δ (ppm): 1.10 to 1.30: m: 3H; 2.20 to 2.4: m: 3H; 3.00 to 3.30: m: 2H; 3.50 to 3.80: m: 2H; 4.80 to 5.00: m: 2H; 6.80 to 8.20: m: 6H; 11.60 to 11.90: m: 1H.

EXAMPLE 8

NMR: δ (ppm): 1.3: td: 3H; 2.0: m: 2H; 2.30: s: 3H; 3.0: s: 3H; 3.10: bt: 2H; 4.2: d: 2H; 4.6: bt: 2H; 6.8 to 8.0: m: 7H.

EXAMPLE 9

NMR: δ (ppm): 1.80: bq: 2H; 2.20: s: 3H; 2.90: s: 3H; 3.0: bt: 2H; 3.90: d: 3H; 4.20: bt: 2H; 6.80 to 8.0: m: 8H.

EXAMPLE 16

NMR: δ (ppm): 1.90 to 2.10: m: 2H; 2.20: s: 3H; 2.60: s: 3H; 2.60 to 3.0: m: 2H; 3.90: s: 3H; 4.5 to 4.7: m: 2H; 6.8 to 7.8: m: 6H.

EXAMPLE 17

NMR: δ (ppm): 1.8: mt: 2H; 2.2: s: 3H; 2.8: s: 3H; 2.95: q: 2H; 3.85: 2s: 3H; 4.2: mt: 2H; 6.6 to 8.0: m: 7H.

EXAMPLE 19

NMR: δ (ppm): 1.8: mt: 2H; 2.2: 2s: 3H; 2.6: s: 6H; 3.0: q: 2H; 4.45: mt: 2H; 6.7 to 7.8: m: 7H; 11.2 to 11.8: 2s: 1H.

EXAMPLE 21

NMR: δ (ppm): 1.2: t: 3H; 1.8: mt: 2H; 2.2: s: 3H; 2.6: s: 6H; 2.9: q: 2H; 4.1: q: 2H; 4.45: mt: 2H; 6.7 to 7.8: m: 7H.

EXAMPLE 22

NMR: δ (ppm): 1.9: mt: 2H; 2.2: s: 3H; 2.65: s: 6H; 3.0: mt: 2H; 4.3 to 4.8: m: 4H; 5.2: mt: 2H; 6: mt: 1H; 6.8 to 7.8: m: 7H.

What is claimed is:

1. A compound of formula:

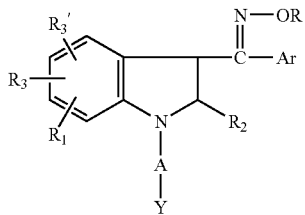

(I)

in which:

Ar represents:
a) a phenyl which is mono-, di- or trisubstituted by one or more groups selected from the following: a halogen atom, a $(C_1–C_4)$alkyl, trifluoromethyl, amino, nitro, hydroxyl, $(C_1–C_4)$alkoxy, $(C_1–C_4)$alkylsulfanyl, or $(C_1–C_4)$alkylsulfonyl group;
b) a naphthyl which is unsubstituted or substituted once or twice by a halogen atom, a $(C_1–C_4)$alkyl group or a trifluoromethyl;

A represents a $C_2–C_6$ alkylene radical;

Y represents a group selected from $SR_4$, $SOR_4$, $SO_2R_4$, $SO_2NR_5R_6$, $N(R_7)SO_2R_4$, $OR_4$ and $NR_7SO_2NR_5R_6$;

R represents hydrogen, a $(C_1–C_4)$alkyl or $(C_2–C_4)$alkenyl group or a group $(C_2–C_4)$alk-$NR_8R_9$;

$R_1$, $R_3$ and $R'_3$ represent each independently of one another hydrogen, a halogen atom or a hydroxyl, $(C_1–C_4)$alkyl, trifluoromethyl or $(C_1–C_4)$alkoxy group;

$R_2$ represents hydrogen or a $(C_1–C_4)$alkyl group;

$R_4$ represents a $(C_1–C_4)$alkyl group or a trifluoromethyl;

$R_5$ and $R_6$ represent each independently hydrogen or a $(C_1–C_4)$alkyl group;

$R_7$ represents hydrogen or a $(C_1–C_4)$alkyl group; and $R_8$ and $R_9$ represent each independently of one another hydrogen or a $(C_1–C_4)$alkyl group, or $R_8$ and $R_9$ together with the nitrogen atom to which they are connected constituted a heterocyclic radical containing from 4 to 7 ring members and being able to contain another heteroatom selected from a nitrogen, oxygen or sulfur atom, unsubstituted or substituted by one or more methyl or methoxy groups; or a salt thereof, or a solvate of said compound or said salt.

2. A compound according to claim 1 of formula (I) in which:

Ar represents:
a) a phenyl which is mono-, di- or trisubstituted by one or more groups selected from the following: a halogen atom, a $(C_1–C_4)$alkyl, trifluoromethyl, amino, nitro, $(C_1–C_4)$alkoxy, $(C_1–C_4)$alkylsulfanyl, or $(C_1–C_4)$alkylsulfonyl group;
b) a naphthyl which is unsubstituted or substituted once or twice by a halogen atom, a $(C_1–C_4)$alkyl group or a trifluoromethyl;

A represents a group $(CH_2)_n$ where n represents 2, 3 or 4;

Y represents a group selected from $SR_4$, $SOR_4$, $SO_2R_4$, $SO_2NR_5R_6$, $N(R_7)SO_2R_4$, and $OR_4$;

R represents hydrogen, a $(C_1–C_4)$alkyl or $(C_2–C_4)$alkenyl group or a group $(C_2–C_4)$alk-$NR_8R_9$;

$R_1$ is in position 7 of the indole ring system and represents a halogen atom or a $(C_1–C_4)$alkyl, trifluoromethyl or $(C_1–C_4)$alkoxy group;

$R_2$ represents hydrogen or a $(C_1–C_4)$alkyl group;

$R_3$ represents hydrogen, a halogen atom or a $(C_1–C_4)$alkyl group;

$R'_3$ is hydrogen;

$R_4$ represents a $(C_1–C_4)$alkyl;

$R_5$ and $R_6$ represent each independently hydrogen or a $(C_1–C_4)$alkyl group;

$R_7$ represents hydrogen or a $(C_1–C_4)$alkyl group; and $R_8$ and $R_9$ represent a $(C_1–C_4)$alkyl or, together with the nitrogen atom to which they are connected, constitute a heterocyclic radical selected from:

azetidinyl, pyrrolidinyl, piperidinyl, perhydroazepinyl, piperazinyl, 4methylpiperazin-1yl, morpholino and thiomorpholine; or a salt thereof, or a solvate of said compound or said salt.

3. A compound according to claim 1 of formula (I) in which:

Ar represents a phenyl which is mono- or disubstituted by a halogen atom, or a methyl, trifluoromethyl, methoxy, methylsulfanyl or methylsulfonyl group;

A represents a group $(CH_2)_n$ where n represents 2, 3 or 4;

Y represents a group $SO_2R_4$, $NHSO_2R_4$;

$R_1$ represents a methyl group or a chlorine or bromine atom in position 7 of the indole ring system;

$R_2$ represents a methyl group;

$R_3$ is hydrogen or $R_3$ is in position 6 of the indole ring system and represents either a chlorine atom or a methyl group;

$R'_3$ is hydrogen;

$R_4$ represents a methyl or ethyl group; and

R represents hydrogen, a methyl or ethyl group or a —(CH$_2$)$_3$N(CH$_3$)$_2$ moiety; or a salt thereof, or a solvate of said compound or said salt.

4. A process for preparing a compound of formula (I) according to claim 1, or a salt thereof, or a solvate of said compound or said salt, wherein an aroylindole derivative of formula:

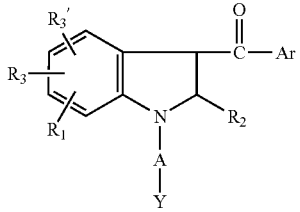

(F)

in which R$_1$, R$_2$, R$_3$, R'$_3$, A, Y and Ar are as defined in claim 1 is treated with a hydroxylamine derivative of formula H$_2$NOR in which R is as defined in claim 1.

5. A pharmaceutical composition comprising as active principle a compound according to claim 1.

6. The pharmaceutical composition according to claim 5, containing from 0.1 to 1000 mg of active principle, in a unit dosage form in which the active principle is mixed with at least one pharmaceutical excipient.

7. A pharmaceutical composition comprising as active principle a compound according to claim 2.

8. A pharmaceutical composition comprising as active principle a compound according to claim 3.

* * * * *